United States Patent [19]
Ries

[11] Patent Number: 4,741,754
[45] Date of Patent: May 3, 1988

[54] PLANT GROWTH STIMULATING COMPOUNDS AND COMPOSITIONS THEREOF

[75] Inventor: Stanley K. Ries, East Lansing, Mich.

[73] Assignee: Michigan State University, East Lansing, Mich.

[21] Appl. No.: 851,070

[22] Filed: Apr. 11, 1986

[51] Int. Cl.$^4$ ............................................. A01N 61/00
[52] U.S. Cl. ......................................... 71/79; 71/122
[58] Field of Search ................................... 71/122, 79

[56] References Cited

U.S. PATENT DOCUMENTS

| | | | |
|---|---|---|---|
| 4,150,970 | 4/1979 | Ries et al. | 71/122 |
| 4,230,485 | 10/1980 | Ohlroggo | 71/122 |
| 4,452,632 | 6/1984 | Nickey et al. | 71/122 |

OTHER PUBLICATIONS

DeWitt et al., Chem. Abst., vol. 91 (1979), 189861z.
Tanaka et al., Chem. Abst., vol. 86 (1977), 152716b.
Ries, CRC Critical Reviews in Plant Science, vol. 2 (1985), pp. 239–285.

Primary Examiner—Catherine L. Mills

[57] ABSTRACT

One or more plant growth stimulating compounds are obtained from plants by treating the plants with 1-triacontanol and extracting the treated plants with a suitable sufficiently polar liquid extractant.

12 Claims, No Drawings

PLANT GROWTH STIMULATING COMPOUNDS AND COMPOSITIONS THEREOF

BACKGROUND OF THE INVENTION

1-Triacontanol ($CH_3(CH_2)_{28}CH_2OH$) is known to be a plant growth regulator capable of utility under widely varying conditions and on a wide variety of crop species (See U.S. Pat. No. 4,150,970).

It has now been discovered that 1-triacontanol when applied to plants elicits in situ formation of one or more recoverable plant growth stimulating compounds in said plants. A suitable extract from plants treated with 1-triacontanol is useful for stimulating plant growth.

SUMMARY OF THE INVENTION

The present invention is directed to a process for recovering, from a suitable plant or part thereof that has been treated with an effective amount of 1-triacontanol, one or more plant growth stimulating compounds in the form of a composition for use in stimulating plant growth comprising intimately contacting at least a portion of said treated plant or part thereof with a sufficiently polar liquid extractant and recovering the liquid to obtain a plant growth stimulating composition that contains one or more plant growth stimulating compounds.

Optionally, the composition may be subjected to concentration and/or fractionation procedures to produce other useful compositions for the stimulation of plant growth. The present invention is also directed to a process for stimulating plant growth comprising the application to a susceptible plant or part thereof of a composition containing an effective amount of the plant growth stimulating compounds. Methods employing concentrates or fractions of said composition are also within the scope of the present invention.

The present invention is also directed to the plant growth stimulating compounds, and compositions containing an effective amount of said compounds, and concentrates or fractions of said compositions.

DETAILED DESCRIPTION OF THE INVENTION

1-Triacontanol (hereinafter "TRIA") is a primary alcohol which is a normal constituent of natural plant waxes. TRIA is quite insoluble in water but can be micro-dispersed in water to form a colloidal dispersion. Colloidal dispersions of TRIA can optionally contain a surfactant such as tallow alkyl sulfate (hereinafter "TAS"). TRIA is slightly soluble in alcohol and is very soluble in organic solvents such as ether chloroform and benzene. Therefore, formation of active emulsions containing the requisite amounts of TRIA is easily accomplished with an organic solvent, water and an emulsifying agent such as "TWEEN 20" (See U.S. Pat. No. 4,150,970, incorporated herein by reference). TRIA increases the growth and sometimes the yield of most crop species. TRIA increases the leaf area, dry weight, total Kjeldahl nitrogen, water soluble protein, reducing sugars and free amino acids within 40 minutes of application in maize (*Zea mays* L) and rice (*Oryza sativa* L). TRIA increases both $Ca^{++}$- and $Mg^{++}$-dependent ATPase activity by 40–60 percent after application of 1.0 microgram ($\mu g$) per liter (1) to cell-free extracts from barley roots. Equimolar concentrations of octacosanol ($CH_3(CH_2)_{26}CH_2OH$), as well as other long chain compounds are not active as plant growth stimulants and in fact inhibit the activity of TRIA. This inhibition occurs even when the two chemicals are applied separately to the shoots and roots of plants.

It has now been discovered that TRIA elicits in situ formation of at least two chemical messengers that move rapidly in plants. The chemical messengers (hereinafter referred to collectively as "TRIM") are compounds that independently and collectively stimulate plant growth. TRIM is present in extracts of suitable plants treated with TRIA. Such as extract having plant growth stimulating activity is a composition within the scope of the present invention that will hereinafter be referred to as "TRIM Extract". At least two TRIM compounds are present in TRIM Extract, one is volatile and one is non-volatile. The TRIM compounds have been shown to be heat stable in that they remain active after heat treatment in an autoclave under typical sterilization temperatures and pressures.

It has also been discovered that extracts of plants treated with octacosanol inhibit the activity of TRIA (i.e., the formation of TRIM), but said extracts have no substantial effect upon the growth stimulating activity of TRIM.

As used herein the term "effective amount" refers to that amount of a substance necessary to produce a desired effect. For example, an effective amount of TRIA is that amount of TRIA that results in production of TRIM when said TRIA is applied to a suitable plant. It has been found that the concentration of TRIA in the compositions to be applied to a suitable plant is critical. On the other hand the total amount of the composition containing TRIA applied to the plant is relatively unimportant. That is, a tank mix composition containing TRIA for field application can be applied to a field crop in minimal amount (e.g., as little as 0.4 grams TRIA per acre for corn seedlings) or the same composition can be sprayed to wet the plants to run-off with little difference, if any, in resulting production of TRIM.

Typically, an effective amount of TRIA when in a colloidal dispersion is from about 0.001 $\mu g$ to about 1,000 $\mu g$ per liter of the composition or formulation to be applied to plants; a preferred effective amount of TRIA is from about 0.1 $\mu g/l$ to about 10 $\mu g/l$; and a most preferred effective amount of TRIA is about 1 $\mu g/l$.

Typically an effective amount of TRIA when in an emulsion is somewhat greater, requiring from about 100 $\mu g$ to about 100,000 $\mu g$ per liter of the diluted formulation or tank mix; a preferred effective amount is about 100 $\mu g/l$ to about 10,000 $\mu g/l$; and a most preferred effective amount is about 1,000 $\mu g/l$.

The behavior of TRIM is similar to that of TRIA in that it has been found that the concentration of TRIM in the compositions be applied to a susceptible plant or plants is critical whereas the total amount of the composition containing TRIM to be applied to a susceptible plant is relatively unimportant. That is, the composition containing TRIM can be applied in very small amounts (e.g., as little as 3.2 grams per acre of crude TRIM) or the same composition, e.g., can be sprayed to wet the plants to run off.

An effective amount of TRIM is that amount of TRIM in the composition containing TRIM necessary to result in growth stimulation of the susceptible plant species. Typically, an effective amount of TRIM in the composition of the present invention is from about 0.2 milligram (mg) to about 2,000 mg dry weight of crude TRIM per liter, of total composition or formulated tank mix thereof. A preferred effective amount of TRIM is the compositions of the present invention is about 100 mg dry weight of crude TRIM per liter. As used herein, the phrase "crude TRIM" refers to TRIM obtained by use of the extraction and purification procedure substantially as described in Example 11 hereof.

In addition to TRIM, the compositions of the present invention contain a suitable diluent such as water or methanol. Also, substantially inert substances may also be present such as impurities resulting in concentration or fractionation procedures. The compositions can also contain additives typically employed in the art such as dispersants and emulsifiers. It is also contemplated that the compositions of the present invention can also contain other biologically active ingredients such as insecticides or herbicides.

Of course, the concentrations and purity of the TRIM in the compositions containing TRIM will have a direct bearing upon the effective amount of said TRIM Extract desired. Much less pure TRIM is required to produce an equivalent plant growth stimulating effect than is required when using crude TRIM.

As used herein, the term, "a suitable plant" is a plant species capable of producing TRIM after the plant has been treated with TRIA. Rice and corn have been shown to be suitable. Other suitable plants include but are not limited to wheat, tomatoes, beans, barley, and potatoes.

As used herein the term "a susceptible plant" is a plant that exhibits growth stimulation after treatment with TRIM or a composition containing TRIM. Susceptible plants are also plants in which it is desired to stimulate growth such as, for example, crop plants. Rice, corn, cucumbers, peppers, carrots and algae have been shown to be susceptible. Examples of other susceptible plants include but are not limited to wheat, tomatoes, beans, barley, potatoes, cotton, soybeans, and alfalfa.

Since TRIM is formed rapidly after treatment of a suitable plant species with TRIA, the time between treatment of said plant with TRIA and initiation of recovery of TRIM is not particularly critical. However, after about 10,000 minutes after TRIA treatment, TRIM recovery can be substantially affected. Therefore, the time between treatment of a suitable plant with TRIA and initiation of the recovery process of TRIM described herein is typically greater than about 1 minute and less than about 10,000 minutes; preferably greater than about 100 minutes and less than about 10,000 minutes.

Suitable recovery procedures for TRIM are those plant tissue extraction procedures typical in the art which result in a plant extract of a suitable plant treated with TRIA. For example, plants or plant parts (e.g., leaves, shoots, roots or any combination thereof) of a suitable plant treated with TRIA are triturated or ground in water, methanol or similar sufficiently polar liquid extractant. The liquid extractant can then be recovered, using standard procedures known in the art, to yield a composition or extract containing one or more plant growth stimulating compounds, i.e., TRIM, that is useful for stimulating the growth of plants. A buffer can be used, if desired, as the liquid extractant or in conjunction with the liquid extractant. In order to prevent possible oxidation of the TRIM, a reducing agent such as 2-mercaptoethanol, ascorbic acid, dithiothreitol, and the like can optionally be employed in the sufficiently polar liquid extractant at concentration levels of from up to about 10 millimolar (mM), preferably about 1 mM. The composition containing the sufficiently polar liquid extractant and TRIM can, desirably, be subjected to further purification and/or concentration procedures. For example, the large particulate and fibrous solids can then be removed physically or mechanically, e.g., by centrifugation or filtration, leaving the liquid containing TRIM. The compositions containing the liquid extractant and TRIM can also optionally be extracted with a water immiscible solvent, for example, chloroform, hexane, or benzene to remove any plant waxes and other solvent soluble materials. After treating the composition with a water immiscible solvent, the non-polar organic phase can then be separated from the polar phase and discarded yielding the extract or composition containing TRIM. It is typically desired to further concentrate and/or partially purify the TRIM from the compositions or by use of standard methods such as column chromatography, (for example, high performance liquid chromatography), selective extraction, fractional distillation, and the like.

The present invention is further illustrated by the following examples; however, these examples should not be interpreted as a limitation upon the scope of the present invention.

Wherein the rice bioassay and the algae bioassay are referred to in the following examples, the procedures set forth as follows were used.

Rice Bioassay

Rice seedlings were grown in a growth chamber and kept constantly moist with distilled water. After 7 days they were transplanted to a Hoagland's water culture medium in specimen cups (4 plants per cup), and grown for an additional 7 days. The plants were sorted for size, and plants of similar size chosen as replicates to test a series of treatments. Each observation consisted of one plant placed in 10 ml of Hoagland's solution, in a 30 ml test tube. The foliage of each plant was sprayed with the extract to be tested, allowed to dry, and the plant in its test tube placed in a growth chamber for 16–24 hours. After this period the rice plants were harvested, weighted and the amount of water used by the seedlings measured after the 24 hours.

Algae Bioassay

*Chlamydomonas rheinhardtii* cultures were grown using a suitable growth medium in the growth chamber at 30° C., on a 24 hour light regime consisting of a 12 hour dark, 12 hour light cycle. Bioassay tests were started 1 hour after initiation of the light cycle. The growth medium containing algae was sparged for 30 seconds with 100 ml of $CO_2$/liter. Algae were pipetted into disposable tubes, and the extracts to be bioassayed added to the tubes. All tubes were then placed in a growth chamber, under the 24 hour light regime. After 16 hours (11 hours light, 5 hours dark) the tubes were centrifuged at 3000 revolutions per minute (rpm) for 15 minutes, water was siphoned off and the algae reconstituted in 80 percent acetone. After centrifuging at 3000 rpm for 5 minutes chlorophyll readings were taken on a spectrophotometer at 652 nanometers (nm). The zero time optical density (O.D.) is subtracted from final chlorophyll readings to estimate increases in growth (as shown by generated chlorophyll) over the 16 hour period.

EXAMPLE 1

A colloidal dispersion of $^{14}C$ radio-labelled TRIA with a specific activity of 23.5 millicurie (mCi) per millimole (m mole) was added to nutrient solutions with 15-day-old rice (cv ESD-1) seedlings. The rice and maize (cv Pioneer 3780) were grown substantially as described in Ries, S. K. and Wert, V. F. J., Plant Growth Regulation, 1, 117–127 (1982). For each representative test, 13 to 15 day-old rice seedlings were grown for the 24 hours of the test in 14.5 centimeter (cm)×2.4 cm test tubes containing 15 milliliter (ml) of half strength Hoagland's nutrient solution number 1. the seedlings were grown at 30° C. (day) and 25° C. (night) temperatures with 16 hours of light and 8 hours of dark, and a light intensity of 300 to 350 micromoles per second per meter ($\mu mol\ s^{-1}m^{-2}$). The observed variance due to plant size was assigned to blocks during the initial plant sorting process. All treatments were randomized within blocks using a random number table. No significant radioactivity could be found in the leaves after 16.7 hours, although significant radioactivity was present in the roots within 10 minutes even after three chloroform washes of the root tissue to remove cuticular waxes.

EXAMPLE 2

To test for the presence of a chemical messenger, the foliage of 13 to 15-day-old rice seedlings was sprayed with 1.0 μg per liter of TRIA formulated as a colloidal dispersion. Control seedlings were sprayed with 0.01 μg per liter of tallow alkyl sulfate (TAS), the surfactant present in the formulation. After 100 minutes, the roots were cut off and ground with a mortar and pestle in 0.02M phosphate buffer containing 1.0 millimole (mM) mercaptoethanol and having a pH of 7.0 at 4.0° C. The extracts were centrifuged at 10,000×gravity (g) for 20 minutes. The supernatant, at rates of 1 to 1000 mg dry weight per liter, was applied back to the roots of rice seedlings growing in nutrient solutions, and to the foliage of maize seedlings growing in the greenhouse. The rice and maize seedlings after 24 hours and 7 days, respectively, were harvested, dried at 70° C. for 14–24 hours and weighed. The growth of both species was stimulated by the crude extract from the TRIA treated plants, but not the crude extract from control plants.

In another test the crude extracts from control and treated plants, respectively, were extracted 3 times with chloroform and the fractions were compared. The activity, as determined by bioassay, was in the aqueous fraction. A dose-response test was conducted on rice seedlings with the water soluble fraction of control and TRIA treated plants. In the 24 hours following treatment rice seedlings treated with the water soluble fraction of TRIA treated plants at concentrations of 28 and 141 mg per liter grew twice as much as the untreated seedlings or plants treated with the same amount of dry matter from control plants. The presence of activity in the aqueous fraction makes it unlikely that the growth stimulation is a result of TRIA contamination. Also, the lack of activity in the controls indicates that TRIM is not indigenous TRIA.

EXAMPLE 3

To examine the speed at which a message is elicited by TRIA, the foliage of rice seedlings was sprayed with 1.0 μg per liter TRIA, the roots cut off with scissors at specified times, frozen, ground at 4° C. and extracted. In these tests, care was taken to protect the roots from spray and to grind the plants so that there was no contamination. Several tests showed that the messengers, i.e., TRIM, moved the 5 to 25 cm from the rice leaves to the roots within one minute of TRIA application.

TRIA was applied to the foliage of rice seedlings as described above and both the shoots and roots were extracted. Significant amounts of TRIM were extracted from both the shoots and roots within 70 seconds of the application of TRIA to the foliage. Apparently TRIM is present in the shoots and TRIA stimulates the formation of TRIM which rapidly increases and is translocated throughout the plant.

EXAMPLE 4

A crude aqueous extract of TRIA treated corn obtained using a procedure substantially similar to that described in Example 2 was put through a polystyrene, Hamilton PRP-1, (4.1 mm×250 mm) column. An analysis of individual chromatograms showed a fraction apparent in the control after 24 minutes that is not present in the TRIM chromatogram after 24 minutes. This chemical in the control may be altered after TRIA application to become one or more of the TRIM messengers. Fractions from control and TRIA treated rice shoots were taken from the polystyrene column, and dried down on a rotary evaporator ("rotavap"). Both rice and algae bioassays of fractions from this column were active (Tables 1 and 2). Earlier results with a high performance liquid chromatograph (HPLC), (Zorbax ODS, $C_{18}$, analytical, 4.6 millimeter (mm)×250 mm column) had given two active regions, and this indicated that there are at least two active materials.

TABLE 1

Response of Algae to Extracts of TRIM From Roots of TRIA Treated Rice Shoots, After Passing Over a Hamilton PRP-1 (polystyrene) Column

| Treatments Fraction | Concentration (mg crude equivalent/l) | O.D. (After Zero time O.D. Subtracted) |
|---|---|---|
| Blank | — | .060 |
| Extract TRIM | 20 | .086 |
| 3 | 20 | .067 |
| 4 | 20 | .062 |
| 5 | 20 | .066 |
| 6 | 20 | .064 |
| 7 | 20 | .067 |
| 8 | 20 | .066 |
| 9 | 20 | .071 |
| 10 | 20 | .074 |
| 17 & 18 | 20 | .066 |
| 19 & 20 | 20 | .065 |
| 21 & 22 | 20 | .067 |
| 25 & 26 | 20 | .064 |
| 27 & 28 | 20 | .064 |
| 29 & 30 | 20 | .070 |
| Least Significant Difference (LSD) 5% | | 0.10 |
| LSD 1% | | 0.14 |

TABLE 2

Response of Rice Seedlings to Extracts of TRIM or TAS From Roots of TRIA or TAS Treated Rice Shoots, After Passing Over a Hamilton PRP-1 (polystyrene) Column

| Treatments Fraction | Retention Time (mins) | Concentration (mg crude extract equivalent/l) | Dry Weight (mg/24 h) | Net Gain (19 h mg/ plant) |
|---|---|---|---|---|
| Blank | — | — | 56.7 | 3.1 |
| TRIM Extract | — | 20 | 68.8 | 15.2 |
| Control | 17 | 100 | 58.7 | 5.1 |

TABLE 2-continued

Response of Rice Seedlings to Extracts of TRIM
or TAS From Roots of TRIA or TAS Treated Rice Shoots,
After Passing Over a Hamilton PRP-1 (polystyrene) Column

| Treatments Fraction | Retention Time (mins) | Concentration (mg crude extract equivalent/l) | Dry Weight (mg/24 h) | Net Gain (19 h mg/plant) |
|---|---|---|---|---|
| Control | 70 | 100 | 59.5 | 5.9 |
| TRIM | 17 | 100 | 67.5 | 13.9 |
| TRIM | 70 | 100 | 68.1 | 14.5 |
| LSD 5% | | | 5.1 | 5.1 |
| LSD 1% | | | 6.8 | 6.8 |

EXAMPLE 5

In many of the bioassays, it was noted that when TRIM extract was injected onto the column, specific activity was reduced. It was thought the fractions could be adsorbed on the glassware during concentration in a rotary evaporator. To alleviate this problem, 30 percent methanol (MeOH) was used to reconstitute the dried samples, instead of water. The vials with the fractions and 30 percent MeOH were allowed to stand in a water bath at 70° C. to drive off the alcohol, and MeOH controls were used in the bioassay. As this did not improve the specific activity the glassware was cleaned thoroughly and silinated before use, but this did not account for the loss of specific activity. The next logical hypothesis was that activity was lost during the drying process. To test this hypothesis, fractions were only partially dried on a rotary evaporator ("rotavap"), and allowed to sit in a water bath (70° C.) to drive off the MeOH residue from the column. However, this did not enhance specific activity. The hypothesis that the activity was adsorbed on the column was then tested. A composition containing TRIM was dried down on the rotavap (in silinated flasks) and tested for activity. Activity was lost, hence adsorption on the column was not the problem. This led to the hypothesis that the active fraction was volatile and was being driven off during the drying or heating processes. Distillation of TRIM extract was carried out and samples were collected for bioassay after distillation; there was activity in the distillate (Table 3). Distilled water was similarly redistilled, as a control, and the distillate was inactive. Fractions of the distillate were collected as they came off the distillation column, and assayed with algae. It was established that the active compound was in the first and second fractions coming off the column (Table 4). In another test the distillate was extracted with ethyl acetate. The algae bioassay showed that the water fraction was still active. This water fraction was redistilled. A portion was dried down on the rotavap and compared to the fraction which was not dried using the algae bioassay. It was evident from these results that the activity is lost during the drying process, because the undried material stimulated algal growth. Clearly, the active moiety of TRIM or one of the active chemicals of TRIM may be distilled from the TRIM extracts. Although this gave a very clean sample for further analysis, it presented a difficulty in the purification process because of the problem of condensing fractions from other analytical procedures, such as HPLC. After many different and unsuccessful approaches it was discovered that the activity was retained in the second residue, if the pH of the first distillate was changed prior to redistilling (Table 5).

TABLE 3

Response of Algae to Extracts of TRIM From Roots of TRIA Treated Rice Shoots After Distillation

| Treatments | Concentration (mg crude dry extract equivalent/l) | O.D. (After Zero Time O.D. Subtracted) |
|---|---|---|
| Blank | — | .034 |
| TRIM Extract | 20 | .061 |
| Distillate | 20 | .050 |
| Distillate | 40 | .061 |
| Distillate | 80 | .060 |
| Residue | 20 | .048 |
| Residue | 40 | .067 |
| Residue | 80 | .085 |
| LSD 5% | | .022 |

TABLE 4

Response of Algae to Extracts of TRIM from Roots of TRIA Treated Rice Shoots After Distillation

| Treatments | Fraction | Concentration (mg crude dry extract equivalent/l) | O.D. (After Zero Time O.D. Subtracted) |
|---|---|---|---|
| Blank | — | — | .029 |
| TRIM Extract | — | 20 | .057 |
| Distillate | 1 | 2 | .045 |
| Distillate | 1 | 20 | .041 |
| Distillate | 2 | 2 | .039 |
| Distillate | 2 | 20 | .046 |
| Distillate | 3 | 20 | .041 |
| Distillate | 4 | 20 | .041 |
| Distillate | 5 | 20 | .029 |
| LSD 5% | | | .013 |
| LSD 1% | | | .018 |

TABLE 5

Response of Algae to Second Distillate and Residue of Extracts of TRIM from Roots of TRIA Treated Rice Shoots at 2 Different pH Values

| Treatments | pH | Concentration (mg crude dry extract equivalent/l) | O.D. After Zero Time O.D. Subtracted |
|---|---|---|---|
| Blank | — | — | .054 |
| TRIM Extract | — | 2.0 | .053 |
| TRIM Extract | — | 0.2 | .056 |
| TRIM Extract | — | 20.0 | .066 |
| Distillate | 11.5 | 0.2 | .059 |
| Distillate | 11.5 | 2.0 | .058 |
| Distillate | 11.5 | 20.0 | .050 |
| Distillate | 3.5 | 0.2 | .058 |
| Distillate | 3.5 | 2.0 | .059 |
| Distillate | 3.5 | 20.0 | .057 |
| Residue | 11.5 | 20.0 | .073 |
| Residue | 3.5 | 20.0 | .083 |
| LSD 5% | | | .007 |
| LSD 1% | | | .009 |

EXAMPLE 6

In another bioassay control extracts and TRIM from rice plant extracts were applied to rice plants. Crude control extracts did not increase the dry weight of the plants and caused the least efficient use of water. Both TRIM extract and the residue from the second distillation (pH 11.8) caused an increase in dry weight and were more efficient users of water (Table 6). On average overall such experiments, raising the pH of the first distillate to 11.8 with $NH_4OH$, and then redistilling, gave a higher specific activity, than lowering the pH to pH 3.2 (Tables 6 and 7). Also when a different lot of rice was treated with TRIA, extracted and distilled, its distillate brought to pH 11.8 (with NH₄OH) and redistilled, this concentrated volatile (second residue) was active. The results showed that the growth of algae was stimulated with increasing concentrations (Table 8).

TABLE 6

Response of Rice Seedlings (20 mg crude dry extract equivalent/l) to Volatile TRIM from Roots of TRIA Treated Rice Shoots that were Redistilled at pH 11.8

| Treatments | Dry Weight (mg/16 hours) | Water Uptake (ml/16 h) | (ul/mg dry wt/16 h) |
|---|---|---|---|
| Control | 6.52 | 4,720 | 724 |
| TAS Crude Control | 5.46 | 4,820 | 883 |
| TRIM distillate (residue 2) | 8.41$^a$ | 5,190$^a$ | 617 |
| TRIM Extract | 11.75$^a$ | 5,240$^a$ | 446 |

$^a$F value for comparison with water and control significant at 1 percent level

TABLE 7

Response of Algae to Volatile TRIM from Roots of TRIA Treated Rice Shoots, that was Distilled at pH Values of 3.2 and 11.8

| Treatments | pH | Concentration (mg crude dry extract equivalent/l) | O.D. (After Zero Time O.D. Subtracted) |
|---|---|---|---|
| Blank | — | — | .059 |
| TRIM Extract | — | 2.0 | .071 |
| Residue | 11.8 | 20.0 | .083 |
| Residue | 3.2 | 20.0 | .074 |
| LSD 5% | | | .011 |
| LSD 1% | | | .014 |

TABLE 8

Dose Response of Volatile TRIM (residue 2, pH 11.8) from a Different Lot of Rice Seedlings Whose Shoots were Treated with TRIA

| Treatments | Concentration (mg crude dry extract equivalent/l) | O.D. (After Zero Time O.D. Subtracted) |
|---|---|---|
| Blank | — | .071 |
| TRIM Extract | 50 | .112 |
| Residue | 10 | .074 |
| Residue | 50 | .076 |
| Residue | 250 | .077 |
| Residue | 1250 | .084 |
| LSD 5% | | .004 |
| LSD 1% | | .006 |

EXAMPLE 7

It was noted that results were marginally better when the algae bioassay was carried out on distillates or second residues immediately after distillation, rather than after 24 or more hours in the freezer. A test was conducted to examine this consisting of distillations conducted with water and TRIM at different pH values. The results showed little differences between the samples, hence freezing of the samples did not cause loss of the volatile compound (Table 9).

TABLE 9

Response of Algae to Different Treatments of the TRIM Distillate from Roots of TRIA Treated Rice Shoots

| Treatments (100 mg crude dry extract equivalent/l) | Distillation | pH | Storage Temperature | O.D. (After Zero Time O.D. Subtracted) |
|---|---|---|---|---|
| Blank | no | — | — | .027 |
| TRIM Extract | no | 7.0 | −16° C. | .053 |
| Water | yes | 4.2 | — | .027 |
| TRIM | yes | 4.2 | +4° C. | .036 |
| TRIM | yes | 4.2 | −16° C. | .034 |
| Water | yes | 11.2 | — | .029 |
| TRIM | yes | 11.2 | +4° C. | .034 |
| TRIM | yes | 11.2 | −16° C. | .033 |
| LSD 5% | | | | .004 |
| LSD 1% | | | | .005 |

EXAMPLE 8

While the various distillation procedures were being carried out, fractions that showed activity on algae or rice, were injected onto the HPLC column (Hamilton PRP-1, 307 mm×7.7 mm), and eluted using 20MeOH:80H₂O. A TRIM extract sample was distilled, the pH of its distillate changed to 11.8 and redistilled. The second residue, which was active on algae, was injected onto the column and two fractions collected. These fractions were distilled again at pH 11.8, to ensure that the volatile stayed as a salt. At a temperature of 95° C., when all of the methanol had evaporated, samples of both the residue and distillate were tested on algae. Both fractions were active, fraction one being more active than fraction two (Table 10).

TABLE 10

Response of Algae to HPLC Fractions of Volatile TRIM from Roots of TRIA Treated Rice Shoots (Residue 2, pH 11.8) After Passed Through a Hamilton Polystyrene PRP-1 Column and Redistilled at pH 11.8

| Treatments | Fraction | Concentration (mg crude dry extract equivalent/l) | O.D. (After Zero Time O.D. Subtracted) |
|---|---|---|---|
| Blank | — | — | .059 |
| Distillate | 1 | 100 | .064 |
| Residue | 1 | 100 | .087 |
| Distillate | 2 | 100 | .038 |
| Residue | 2 | 100 | .072 |
| LSD 5% | | | .011 |
| LSD 1% | | | .014 |

EXAMPLE 9

In the previous Examples, despite some inconsistencies with the volatile, the first residue of TRIM extract is always active. Based on this data it was decided to concentrate first on identification of the active moiety in this non-volatile residue. This material was injected onto the HPLC column (Hamilton PRP-1, 307 mm×7.7 mm), fractions collected and assayed. The active fractions (1 and 2) of TRIM and corresponding fractions of the control, respectively, were reinjected on the column and further separated into 5 separate fractions. The assays of these fractions showed that Fraction A of TRIM was active, while the control fractions showed no activity (Table 11).

TABLE 11

Response of Algae to HPLC Fractions of TRIM and TAS Residues from Roots of TRIA or TAS Treated Rice Shoots After the Volatile TRIM was Removed

| Treatments (40 mg crude dry extract equivalent/l) | Fraction | TRIM O.D. (After Zero Time O.D. Subtracted) | TAS Control O.D. (After Zero Time O.D. Subtracted) |
|---|---|---|---|
| Blank | — | .024 | .051 |
| Total residue | — | .054 | .067 |
| Residue | A | .041 | .058 |
| Residue | B | .025 | .057 |
| Residue | C | .026 | .052 |
| Residue | D | .024 | .046 |
| Residue | E | .022 | .044 |
| LSD 5% | | .004 | .010 |
| LSD 1% | | .005 | .013 |

EXAMPLE 10

The active residue of TRIM was separated using a gradient of 0 to 100 percent MeOH and the balance water. Ten fractions were collected and bioassayed with the algae. Fractions 1 to 5 were highly active (Table 12). Residue 1 of TAS control, which had previously shown some activity was similarly run on the column, 8 fractions collected, and assayed on the algae, but none of these fractions were active (Table 12).

The highly active fractions 1 to 5 from TRIM (Table 12), were then combined and rerun on a $C_{18}$ (Zorbax) column at 25MeOH:75H$_2$O. Fraction 2 from this test was highly active (Table 13).

TABLE 12

Response of Algae to HPLC Fractions of TRIM and TAS Control Residues from Roots of TRIA and TAS Treated Rice Shoots, after the Volatile was Removed

| Treatments (40 mg crude dry extract equivalent/l) | Fractions | TRIM O.D. (After Zero Time O.D. Subtracted) | TAS Control O.D. (After Zero Time O.D. Subtracted) |
|---|---|---|---|
| Blank | — | .052 | .049 |
| Crude extract | — | .084 | .063 |
| Residue | 1 | .065 | .050 |
| Residue | 2 | .065 | .054 |
| Residue | 3 | .065 | .047 |
| Residue | 4 | .061 | .048 |
| Residue | 5 | .057 | .049 |
| Residue | 6 | .054 | .049 |
| Residue | 7 | .053 | .046 |
| Residue | 8 | .055 | .049 |
| Residue | 9 | .056 | — |
| Residue | 10 | .053 | — |
| LSD 5% | | .004 | .007 |
| LSD 1% | | .006 | .009 |

TABLE 13

Response of Algae to Fractions of Non-Volatile TRIM Residue from Roots of TRIA Treated Rice Shoots After Passing Through Polystyrene (Hamilton PRP-1) and $C_{18}$(Zorbax) Columns

| Treatments (40 mg crude dry extract equivalent/l) | Fraction | O.D. After Zero Time O.D. Subtracted |
|---|---|---|
| Blank | — | .052 |
| Fractions 1 to 5 from polystyrene column | 1 to 5 combined | .072 |
| Fractions 1 to 4 on $C_{18}$ column | 1 | .052 |
| Fractions 1 to 4 on $C_{18}$ column | 2 | .063 |
| Fractions 1 to 4 on $C_{18}$ column | 3 | .052 |
| Fractions 1 to 4 on $C_{18}$ column | 4 | .053 |
| LSD 5% | | .006 |
| LSD 1% | | .008 |

EXAMPLE 11

To obtain TRIM for certain Examples, the following purification scheme was used.

Rice foliage is treated for 100 minutes with 1.0 µg/liter of TRIA. Roots are removed and ground in 20 mM phosphate buffer (pH 7.0 and 4.0 ml/g fresh weight). After centrifugation for 30 minutes at 10,000×g, the supernatant is extracted 3 times with equal volumes of chloroform. The chloroform is removed by purging with $N_2$. The anion fraction is obtained by passing through a column of a styrene-divinylbenzene copolymer ion-exchange resin (Dowex ®)-1×8-100 (OH$^-$). The anion fraction is removed from column with 0.25M HCl and lyophilized.

The lyophilized anion fraction is then reconstituted in water and passed through a column of a styrene-divinylbenzene copolymer ion-exchange resin (Dowex ®)-1×8-100 (CH$_3$COO$^-$). The non-absorbed fraction is then collected, flash evaporated and reconstituted in water. The reconstituted fraction thus obtained is then passed through a Sephadex ® G-10 column using water as the solvent. The active fraction from the Sephadex ® G-10 column is the third $A_{260}$ peak. The active fraction is then collected and flash evaporated and reconstituted in water. The reconstituted active fraction is then subjected to HPLC using a Zorbax ODS, $C_{18}$, analytical, 4.6 mm×250 mm column. The fraction collected at 9 to 15 minutes (min) (at 1 ml per min flow rate and reading with $A_{254}$) is then flash evaporated and reconstituted in water. The reconstituted fraction thus obtained is then again subjected to HPLC using a Zorbax ODS, $C_{18}$, analytical, 4.6 mm×250 mm column (at 1 ml per min flow rate and reading with $A_{254}$). The fraction obtained between 9 min and 9 min, 30 seconds is collected and flash evaporated. The fraction thus obtained is crude TRIM. The crude TRIM thus obtained is reconstituted in water at a desired concentration for use in application to plants.

EXAMPLE 12

TRIM, obtained substantially as described in Example 11, was applied to wheat and the results are in Table 14.

The wheat was soft, white, winter wheat in plots 6 meters long, 4 rows wide, 17 centimeter spacing. The center two rows were harvested for analysis.

TABLE 14

Response of Wheat to a Single Applicaton of TRIM

| Treatments Crude TRIM (mg/l) | Yield kilograms/hectare (kg/ha) | Seed wt (mg/seed) |
|---|---|---|
| 0 | 4,762 | 4.40 |
| 1 | 5,049[a] | 4.42 |
| 10 | 5,030[a] | 4.52 |
| 100 | 5,080[a] | 4.47 |

[a]F value for comparison with control significant at 5% level

EXAMPLE 13

TRIM, as well as other substances, was applied to 18-day-old rice seedlings and the results are in Tables 15 and 16.

OCTAM refers to an extract of rice treated with Octacosanol.

TABLE 15

Response of 18-day-old Rice Seedlings to Extracts (TRIM and OCTAM) Elicited by TRIA and Octacosanol and Mixtures of these with TRIA and Octacosanol

| Treatments (applied in nutrient solution) | | Dry weight after 24 hour in mg | | | | % Increase |
|---|---|---|---|---|---|---|
| Chemical (1.0 μg/l) | Extract (19 mg/l) | Root | Shoot | Total | Increase in 24 hour | in Dry Weight Over Average of Control[b] |
| Zero time | | 11.1 | 27.6 | 38.7 | | |
| Octacosanol | | 12.3 | 34.5 | 46.8 | 8.1 | |
| | OCTAM[a] | 11.9 | 32.4 | 44.3 | 5.6 | |
| TRIA | | 13.8 | 35.4 | 49.3 | 10.6 | 56 |
| TRIA | OCTAM | 12.2 | 33.8 | 46.0 | 7.3 | 7 |
| | TRIM[a] | 13.9 | 35.7 | 49.6 | 10.9 | 60 |
| Octacosanol | TRIM | 13.8 | 38.4 | 52.2 | 13.5 | 99 |
| LSD 5% | | 1.2 | 2.0 | 3.4 | 3.4 | |
| LSD 1% | | 1.6 | 2.7 | 4.6 | 4.5 | |

[a]TRIM and OCTAM are water soluble fractions after 3 chloroform extractions.
[b]Average of Control was 6.8

TABLE 16

Response of Rice Seedlings to OCTAM[a], TRIM[a] and Mixtures of the Two

| Controls | Rice Root Extract (19 mg dry extract/l) Extract | Increase in dry weight in 24 hr (mg/plant) | (% increase over average of controls) |
|---|---|---|---|
| Untreated | None | 7.04 | — |
| Tallow alkyl sulfate | None | 9.16 | |
| | TRIM | 14.00 | 73 |
| | OCTAM | 9.16 | 13 |
| | TRIM + OCTAM | 14.52 | 79 |
| LSD 5% | | 3.64 | |
| LSD 1% | | 3.57 | |

[a]TRIM and OCTAM are water soluble fractions after 3 chloroform extractions.

EXAMPLE 14

The response of various types of plants under various conditions to application of TRIM, obtained substantially as described in Example 11, is shown in Tables 17 through 25.

Unless indicated otherwise, the methods and techniques used were substantially as described in U.S. Pat. No. 4,150,970, incorporated herein by reference.

TABLE 17

Response of 19-day-old Rice Seedlings, 24 hours after Treatment, to TRIM when added with Octacosanol in Nutrient Solution

| Treatments Chemical | Dry weight after 24 hr | |
|---|---|---|
| | (ug/liter) | mg/seedling |
| Control | — | 104.0 |
| Octacosanol | 1.0 | 104.9 |
| TRIM (anion fraction) | 1000 | 112.9 |
| Octacosanol + TRIM | 1.0 + 1000 | 113.1 |
| LSD 5% | | 5.2 |
| LSD 1% | | 7.1 |

TABLE 18

Response of Corn Seedlings to Multiple Sprays of TRIM

| Date of Application (20 mg dry wt/liter anion fraction) | Date of Harvest 4/16 (mg dry wt per shoot) | 4/23 | Average % increase over control |
|---|---|---|---|
| Dry Control | 223 | 1,436 | |
| 4/10 | 249 | 1,471 | 7 |
| 4/12 | 243 | 1,525 | 8 |
| 4/14 | 246 | 1,480 | 6 |
| 4/10, 4/12, 4/14, 4/16, 4/18, 4/20 | 265 | 1,590 | 15 |
| LSD 5% | 20 | 94 | |
| LSD 1% | 28 | | |

TABLE 19

Response of Cucumbers and Peppers to TRIM

| Treatments TRIM Fraction | mg dry wt equivalent/liter | Cucumbers (25 days mg/shoot) | Peppers (25 days mg/shoot) |
|---|---|---|---|
| Dry control | — | 698 | 87 |
| Anion | 20 | 744 | 107[b] |
| Water | 20 (Multiple Sprays) | 774[a] | 104[b] |
| Water | 200 | 734 | 107[b] |

[a]F value for comparison with controls significant at 5% level
[b]F value for comparison with controls significant at 1% level

TABLE 20

Response of Rice and Corn Seedlings to TRIM (19 mg dry weight per liter) from Rice Roots after Different Times of Exposure of Shoots to TRIA

| Treatments | | | Increase in growth in 24 hr | | |
|---|---|---|---|---|---|
| | | | Rice (18-days-old) | | Corn (8-days-old) |
| Rice Root Extract | Foliar tmt ($\mu$g/l) | Time (seconds) | Dry Weight (mg/plant) | Water uptake[c] (g/plant) | Dry Weight (mg/shoot) |
| TAS control | 0.01 | 135 | 11.9 | 7.87 | 20.12 |
| TRIA | 1.00 | 0 | 11.8 | 7.58 | 20.08 |
| TRIA | 1.00 | 5 | 10.7 | 7.67 | 21.29 |
| TRIA | 1.00 | 15 | 11.0 | 7.68 | 21.88 |
| TRIA | 1.00 | 45 | 15.2[a] | 8.43[a] | 20.58 |
| TRIA | 1.00 | 135 | 17.2[a] | 8.98[a] | 26.08[a] |

[a]F value for comparison with control and 0, 5, and 15 seconds treatments significant at 1% level.
[b]Correlation coefficient for % dry weight increase with time: r = 0.94, y = 0.51 + 0.36x.
[c]Correlation coefficient for water uptake with time: r = 0.96*, y = 0.89 + 0.14x.

TABLE 21

Comparison of One Versus Two Sprays of TRIA and TRIM Applied to 13-day Old Cucumbers - Cucumbers Were Harvested When 22-days Old

| Treatments | 13 days (mg/shoot) | % Increase Over Control | 13 and 15 days (mg/shoot) | % Increase Over Control |
|---|---|---|---|---|
| Control | 722 | | 780 | |
| TRIA (1.0 $\mu$g/liter) | 818 | 6 | 792 | 2 |
| TRIM (20 mg/liter) | 862[a] | 12 | 953[a] | 23 |

[a]F value for difference from control significant at 5% level.

TABLE 22

Response of 13-day-old Corn Seedlings to Multiple Applications of TRIM 7 Days After Treatment

| Treatments | Number of Applications | Rank 1 Day | Rank 2 Days | Fresh (mg/seedling) | Dry | % Increase Over Control |
|---|---|---|---|---|---|---|
| Dry Control | 0 | 1.4 | 1.4 | 4,870 | 448 | |
| TRIA | 1 | 3.4 | 2.6 | 5,050 | 472 | 5.4 |
| TRIM | 1 | 3.0 | 2.4 | 5,018 | 468 | 4.5 |
| TRIM | 5 | 2.1 | 3.3 | 5,312 | 495 | 10.5 |
| LSD 5% | | 1.0 | 1.2 | 260 | 22 | |
| LSD 1% | | 1.3 | 1.6 | | 32 | |

TABLE 23

Response of 18-day-old Rice Seedlings 24 hr After Foliar Application of Different Ionic Fractions of Rice Roots from Plants Whose Foliage was Treated with TRIA for 100 Minutes

| Crude Extract Fraction (from 100 mg dry wt/l) | Dry Weight Increase in 24 hr (mg/seedling) | (% increase over control) |
|---|---|---|
| Dry Control | 5.7 | |
| Surfactant Control | 6.2 | 9 |
| Total | 9.3 | 63 |
| Neutral | 5.9 | 4 |
| Cation | 7.7 | 35 |
| Anion | 9.5 | 67 |
| LSD 5% | 2.5 | |
| LSD 1% | 3.3 | |

TABLE 24

Response of 19-day-old Carrots to TRIA, TRIM and Multiple Sprays of TRIM

| Treatments | Time of Application | Dry Weight 13 days after Treatment (mg/plant) | (% increase over control) |
|---|---|---|---|
| Control | — | 221 | |
| TRIA (1.0 $\mu$g/l) | 5/22 | 250 | 13 |
| TRIM (20 mg/l) | 5/22 | 250 | 13 |
| TRIM (20 mg/l) | 5/22, 5/25, 5/29 | 266 | 20 |
| LSD 5% | | 24 | |
| LSD 1% | | 33 | |

TABLE 25

Response of 13-day-old Corn Seedlings to Multiple Applications of TRIM 7 Days After Treatment

| Treatments | Number of Applications | Rank 1 Day | Rank 2 Days | Fresh (mg/seedling) | Dry | % Increase Over Control |
|---|---|---|---|---|---|---|
| Dry Control | 0 | 1.4 | 1.4 | 4,870 | 448 | |
| TRIA | 1 | 3.4 | 2.6 | 5,050 | 472 | 5.4 |
| TRIM | 1 | 3.0 | 2.4 | 5,018 | 468 | 4.5 |
| TRIM | 5 | 2.1 | 3.3 | 5,312 | 495 | 10.5 |
| LSD 5% | | 1.0 | 1.2 | 260 | 22 | |
| LSD 1% | | 1.3 | 1.6 | | 32 | |

EXAMPLE 15

TRIA treated rice seedlings were extracted with methanol and butanol and the resulting extracts were compared to crude TRIM extracted with water using the algae bioassay. The results are in Tables 26 and 27.

TABLE 26

Response of Algae to Extracts of TRIA Treated Rice Seedlings, After Soxhlet Extraction with Methanol and Reconstitution in Water

| Treatments | Conc. (mg crude equivalent) | O.D. zero time subtracted | % increase over control |
|---|---|---|---|
| Blank | — | .035 | |
| Crude TRIM | 20 | .055 | 57 |
| Crude TRIM | 200 | .087 | 148 |
| Methanol extract | 20 | .061 | 74 |
| Methanol extract | 200 | .073 | 108 |
| LSD 5% | | .014 | |
| 1% | | .019 | |

TABLE 27

Response of Algae to Extracts of TRIA, Treated Rice Seedlings, After Soxhlet Extraction with Methanol and Reconstitution in Water

| Treatments | Conc. (mg crude equivalent) | O.D. zero time substracted) | % increase over control |
|---|---|---|---|
| Blank | — | .043 | — |
| Crude TRIM | 20 | .060 | 39 |
| Crude TRIM | 200 | .106 | 147 |
| Crude TRIM | 2000 | .150 | 249 |
| Butanol extract | 20 | .042 | 0 |
| Butanol extract | 200 | .036 | 0 |
| Butanol extract | 2000 | .094 | 2 |
| LSD 5% | | .016 | |
| 1% | | .022 | |

What is claimed is:

1. A method for stimulating the growth of plants which comprises applying to said plants, a plant growth stimulating amount of a composition containing one or more plant growth stimulating compounds, said composition having been recovered from plants or plant parts which have been treated with a plant growth stimulating amount of 1-triacontanol, by contacting said treated plant or plant parts with a polar liquid extractant to obtain said composition containing one or more plant growth stimulating compounds.

2. A method as defined in claim 1 wherein the composition is further treated with a water immiscible solvent to remove plant waxes and other solvent soluble materials.

3. A method as defined in claim 2 wherein the water immiscible solvent is chloroform, hexane or benzene.

4. A method as defined in claim 2 including further purification of the composition by the use column chromatography.

5. A method as defined in claim 2 including further purification of the composition by the use of fractional distillation.

6. A method as defined in claim 1 wherein the polar liquid extractant is water or methanol.

7. A method as defined in claim 1 wherein the plant treated with 1-triacontanol is selected from the group consisting of rice, corn, wheat, tomatoes, beans, barley and potatoes.

8. The method as defined in claim 7 wherein the plant is rice or corn.

9. The method as defined in claim 1 wherein the composition contains from about 0.2 mg to about 2,000 mg of crude TRIM per liter of total composition.

10. The method as defined in claim 9 wherein the composition contains about 20 mg of crude TRIM per liter of total composition.

11. The method as defined in claim 1 wherein the plant treated with the composition is selected from the group consisting of rice, corn, cucumbers, peppers, carrots, algae, wheat, tomatoes, beans, barley, potatoes, cotton, soybeans and alfalfa.

12. The method as defined in claim 11 wherein the plant is selected from the group consisting of rice, corn, cucumbers, peppers, carrots and algae.

* * * * *